United States Patent
Karube et al.

(10) Patent No.: US 10,392,326 B2
(45) Date of Patent: Aug. 27, 2019

(54) METHOD FOR PRODUCING FLUORINE-CONTAINING COMPOUND

(71) Applicant: DAIKIN INDUSTRIES, LTD., Osaka (JP)

(72) Inventors: Daisuke Karube, Osaka (JP); Takehiro Chaki, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/544,987

(22) PCT Filed: Jan. 19, 2016

(86) PCT No.: PCT/JP2016/051423
§ 371 (c)(1),
(2) Date: Jul. 20, 2017

(87) PCT Pub. No.: WO2016/117551
PCT Pub. Date: Jul. 28, 2016

(65) Prior Publication Data
US 2018/0273448 A1  Sep. 27, 2018

(30) Foreign Application Priority Data

Jan. 21, 2015 (JP) .................. 2015-009603

(51) Int. Cl.
*C07C 17/20* (2006.01)
*C07C 17/25* (2006.01)
(Continued)

(52) U.S. Cl.
CPC ............ *C07C 17/20* (2013.01); *C07C 17/206* (2013.01); *C07C 17/25* (2013.01); *C07B 61/00* (2013.01)

(58) Field of Classification Search
CPC .............................. C07C 17/25; C07C 17/206
See application file for complete search history.

(56) References Cited

U.S. PATENT DOCUMENTS

| 6,362,383 B1 | 3/2002 | Wilmet et al. |
| 2011/0105807 A1 | 5/2011 | Kopkalli et al. |

(Continued)

FOREIGN PATENT DOCUMENTS

| EP | 0 939 071 | 9/1999 |
| JP | 2002-504528 | 2/2002 |

(Continued)

OTHER PUBLICATIONS

WO2015005322A1, Jan. 15, 2011, English translation (Year: 2015).*

(Continued)

*Primary Examiner* — Medhanit W Bahta
(74) *Attorney, Agent, or Firm* — Wenderoth, Lind & Ponack, L.L.P.

(57) ABSTRACT

The present invention provides an economically advantageous method for efficiently producing a fluorine-containing compound while ensuring high conversion of the starting compound, reducing production of 245cb, and reducing equipment costs and energy costs. Specifically, the present invention provides a method for producing a fluorine-containing compound represented by Formula (3): $CF_3CFY_nCH_2Z_n$ (wherein n is 0 or 1, one of Y and Z is H, and the other is F or Cl) by successively reacting at least one chlorine-containing compound selected from the group consisting of chlorine-containing fluoroalkane represented by Formula (1): $CX_3CHClCH_2Cl$ (wherein X is independently F or Cl, with the proviso that at least one X is F) and chlorine-containing fluoroolefin represented by Formula (2): $CX_3CCl=CH_2$ (wherein X is independently F or Cl, with the proviso that at least one X is F) with anhydrous hydrogen fluoride in the presence of a fluorination catalyst, wherein the concentration of hydrogen chloride in a reactor inlet gas is not less than 0.01 vol % and not more than 10 vol %.

16 Claims, 1 Drawing Sheet

(51) Int. Cl.
*C07C 21/18* (2006.01)
*C07B 61/00* (2006.01)

(56) References Cited

U.S. PATENT DOCUMENTS

| | | | |
|---|---|---|---|
| 2012/0184785 A1* | 7/2012 | Cottrell | C07C 17/087 570/153 |
| 2014/0012047 A1* | 1/2014 | Merkel | C07C 17/087 570/155 |
| 2014/0275653 A1 | 9/2014 | Pigamo et al. | |
| 2014/0350312 A1 | 11/2014 | Yang et al. | |
| 2016/0152534 A1* | 6/2016 | Chaki | C07C 17/206 570/160 |

FOREIGN PATENT DOCUMENTS

| | | |
|---|---|---|
| JP | 2010-043080 | 2/2010 |
| JP | 2011-529447 | 12/2011 |
| JP | 2012-519654 | 8/2012 |
| JP | 2012-524026 | 10/2012 |
| JP | 2013-519629 | 5/2013 |
| JP | 2013-537167 | 9/2013 |
| JP | 2013-237677 | 11/2013 |
| JP | 2014-530088 | 11/2014 |
| JP | 2014-532046 | 12/2014 |
| WO | 2008/040969 | 4/2008 |
| WO | 2008/054781 | 5/2008 |
| WO | 2009/003084 | 12/2008 |
| WO | 2010/013577 | 2/2010 |
| WO | 2010/101198 | 9/2010 |
| WO | 2010/123154 | 10/2010 |
| WO | 2011/077192 | 6/2011 |
| WO | 2011/099605 | 8/2011 |
| WO | 2011/110889 | 9/2011 |
| WO | 2012-009114 | 1/2012 |
| WO | 2012/057367 | 5/2012 |
| WO | 2014/025065 | 2/2014 |
| WO | 2015/005322 | 1/2015 |

OTHER PUBLICATIONS

International Search Report dated Apr. 26, 2016 in International (PCT) Application No. PCT/JP2016/051423.
Extended European Search Report dated Sep. 7, 2018 in corresponding European Application No. 16740158.7.

* cited by examiner

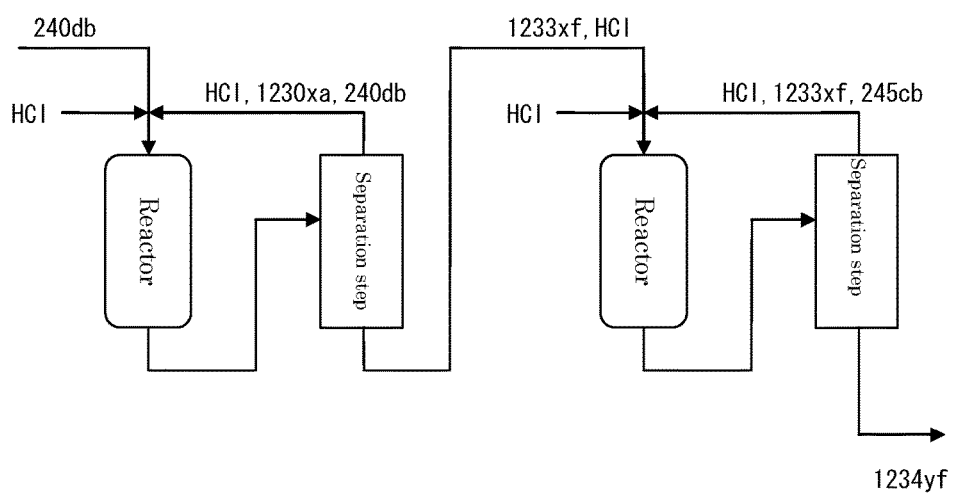

METHOD FOR PRODUCING FLUORINE-CONTAINING COMPOUND

TECHNICAL FIELD

The present invention relates to a method for producing fluoropropene.

BACKGROUND ART

The process of producing 2,3,3,3-tetrafluoropropene (1234yf) from 2-chloro-3,3,3-trifluoropropene (1233xf) through a fluorination reaction is useful as a method for producing 1234yf because 1233xf can be easily produced from chlorine-containing compounds, such as 1,1,1,2,3-pentachloropropane (240db) or 1,1,2,3-tetrachloropropene (1230xa).

However, in the process of converting 1233xf into 1234yf through a gas-phase fluorination reaction, the conversion into 1234yf in the reaction is low; therefore, the reaction often requires a large production facility, a facility or process of recycling unreacted raw materials, and the like, thereby increasing the production costs.

Further, a previously known method for producing 1234yf specifies that hydrogen chloride produced as a by-product is separated, i.e., the hydrogen chloride as a by-product is not returned to the reactor; such separation of hydrogen chloride requires another facility separated from the reactor. Moreover, the method must be performed under severe conditions, such as a high pressure condition of about 0.5 MPaG or more, a low temperature condition of about −40° C. or less, and the like, thereby increasing the load and costs of equipment.

Further, when 1233xf is converted to 1234yf by a gas-phase fluorination reaction, 1,1,1,2,2-pentafluoropropane (245cb) is obtained as a by-product in which hydrogen fluoride is added to the desired product. 1,1,1,2,2-pentafluoropropane can be returned to 1234yf through dehydrofluorination; however, this requires another reaction step for dehydrofluorination, or a dehydrofluorination step after returning the by-product to the original reactor. Therefore, improvement is necessary in terms of equipment costs, energy costs, and production efficiency.

CITATION LIST

Patent Documents

Patent Document 1: WO2008/054781A
Patent Document 2: WO2011/077192A
Patent Document 3: WO2010/123154A
Patent Document 4: WO2009/003084A

SUMMARY OF INVENTION

Technical Problem

In the production method of the prior art, hydrogen chloride is not included in the reaction step; further, when hydrogen chloride is generated as a by-product, the hydrogen chloride is separated by using a separation device, which must be operated under severe conditions. Further, when an overly fluorinated compound or the like is generated as a by-product, another reaction step is necessary to convert it into the desired product. Due to such circumstances, equipment costs and energy costs were high.

The present invention was made in light of current circumstances of the prior art and a major object of the invention is to provide an economically advantageous method for efficiently producing a fluorine-containing compound represented by Formula (3): $CF_3CFY_nCH_2Z_n$ (wherein n is 0 or 1, one of Y and Z is H, and the other is F or Cl) by successively reacting at least one chlorine-containing compound selected from the group consisting of chlorine-containing fluoroalkane represented by Formula (1): $CX_3CHClCH_2Cl$ (wherein X is independently F or Cl, with the proviso that at least one X is F) and chlorine-containing fluoroolefin represented by Formula (2): $CX_3CCl\!=\!CH_2$ (wherein X is independently F or Cl, with the proviso that at least one X is F) with anhydrous hydrogen fluoride in the presence of a fluorination catalyst, while ensuring high conversion of the starting compound, reducing production of by-product, and reducing equipment costs and energy costs.

Solution to Problem

In order to attain the above object, the present inventors conducted extensive research and found that, by using a process of incorporating a specific ratio of hydrogen chloride in the reactor inlet, the method for producing a fluorine-containing compound represented by Formula (3): $CF_3CFY_nCH_2Z_n$ (wherein n is 0 or 1, one of Y and Z is H, and the other is F or Cl) by successively reacting at least one chlorine-containing compound selected from the group consisting of chlorine-containing fluoroalkane represented by Formula (1): $CX_3CHClCH_2Cl$ (wherein X is independently F or Cl, with the proviso that at least one X is F) and chlorine-containing fluoroolefin represented by Formula (2): $CX_3CCl\!=\!CH_2$ (wherein X is independently F or Cl, with the proviso that at least one X is F) with anhydrous hydrogen fluoride in the presence of a fluorination catalyst can be performed while ensuring high conversion of the starting compound, reducing production of by-products, and reducing equipment costs and energy costs. The present invention was completed through further research based on the above finding.

Specifically, the present invention provides the following methods for producing fluoroolefin.

Item 1: A method for producing a fluorine-containing compound represented by Formula (3): $CF_3CFY_nCH_2Z_n$ (wherein n is 0 or 1, one of Y and Z is H, and the other is F or Cl) by successively reacting at least one chlorine-containing compound selected from the group consisting of chlorine-containing fluoroalkane represented by Formula (1): $CX_3CHClCH_2Cl$ (wherein X is independently F or Cl, with the proviso that at least one X is F) and chlorine-containing fluoroolefin represented by Formula (2): $CX_3CCl\!=\!CH_2$ (wherein X is independently F or Cl, with the proviso that at least one X is F) with anhydrous hydrogen fluoride in the presence of a fluorination catalyst, wherein the concentration of hydrogen chloride in a reactor inlet gas is not less than 0.01 vol % and not more than 10 vol %.

Item 2: The method for producing a fluorine-containing compound according to Item 1, wherein the concentration of hydrogen chloride in the reactor inlet gas is not less than 0.01 vol % and not more than 3 vol %.

Item 3: The method for producing a fluorine-containing compound according to Item 1 or 2, wherein the chlorine-containing compound is at least one compound selected from the group consisting of 2,3-dichloro-1,1,1-trifluoropropane and 2-chloro-3,3,3-trifluoropropene, and the fluorine-containing compound is 1,1,1,2,2-pentafluoropropane, 1,1,1,2,3-pentafluoropropane, or 2,3,3,3-tetrafluoropropene.

Item 4: The method for producing a fluorine-containing compound according to any one of Items 1 to 3, wherein the chlorine-containing compound is 2-chloro-3,3,3-trifluoropropene.

Item 5: The method for producing a fluorine-containing compound according to any one of Items 1 to 4, wherein the fluorine-containing compound is 2,3,3,3-tetrafluoropropene.

Item 6: A method for producing a fluorine-containing compound represented by Formula (3): $CF_3CFY_nCH_2Z_n$ (wherein n is 0 or 1, one of Y and Z is H, and the other is F or Cl) by reacting at least one chlorine-containing compound selected from the group consisting of chlorine-containing fluoroalkane represented by Formula (1): $CX_3CHClCH_2Cl$ (wherein X is independently F or Cl, with the proviso that at least one X is F) and chlorine-containing fluoroolefin represented by Formula (2): $CX_3CCl=CH_2$ (wherein X is independently F or Cl, with the proviso that at least one X is F) with anhydrous hydrogen fluoride in the presence of a fluorination catalyst, the method further comprising separating a component containing unreacted raw material from a reactor outlet gas and circulating the component in the reactor inlet to subject the component again to the reaction, wherein the concentration of hydrogen chloride in a circulating gas is not less than 0.01 vol % and not more than 10 vol %.

Item 7: The method for producing a fluorine-containing compound according to Item 6, wherein the concentration of hydrogen chloride in the circulating gas is not less than 0.01 vol % and not more than 3 vol %.

Item 8: The method for producing a fluorine-containing compound according to Item 6 or 7, wherein the chlorine-containing compound is at least one compound selected from the group consisting of 2,3-dichloro-1,1,1-trifluoropropane and 2-chloro-3,3,3-trifluoropropene, and the fluorine-containing compound is 1,1,1,2-tetrafluoro-2-chloropropane, 1,1,1,2,2-pentafluoropropane, or 2,3,3,3-tetrafluoropropene.

Item 9: The method for producing a fluorine-containing compound according to any one of Items 6 to 8, wherein the chlorine-containing compound is 2-chloro-3,3,3-trifluoropropene.

Item 10: The method for producing a fluorine-containing compound according to any one of Items 6 to 9, wherein the fluorine-containing compound is 2,3,3,3-tetrafluoropropene.

Item 11: The method for producing a fluorine-containing compound comprising the steps of:

(a) obtaining a reactor outlet gas containing at least one chlorine-containing compound selected from the group consisting of chlorine-containing fluoroalkane represented by Formula (1): $CX_3CHClCH_2Cl$ (wherein X is independently F or Cl, with the proviso that at least one X is F) and chlorine-containing fluoroolefin represented by Formula (2): $CX_3CCl=CH_2$ (wherein X is independently F or Cl, with the proviso that at least one X is F) and hydrogen chloride by reacting at least one chlorine-containing compound selected from the group consisting of chlorine-containing alkane represented by Formula (4): $CX_3CHClCH_2Cl$ (wherein X is independently F or Cl, with the proviso that at least one X is Cl), chlorine-containing olefin represented by Formula (5): $CX_3CCl=CH_2$ (wherein X is independently F or Cl, with the proviso that at least one X is Cl), and chlorine-containing olefin represented by Formula (6): $CX_2=CClCH_2X$ (wherein X is independently F or Cl, with the proviso that at least one X is Cl) with anhydrous hydrogen fluoride in the presence of a fluorination catalyst;

(b) adjusting the concentration of the hydrogen chloride in the reactor outlet gas obtained in step (a) to not less than 0.01 vol % and not more than 10 vol % to obtain a reactor inlet gas to be subjected to a reactor for obtaining a fluorine-containing compound represented by Formula (3): $CF_3CFY_nCH_2Z_n$ (wherein n is 0 or 1, one of Y and Z is H, and the other is F or Cl); and (c) producing the fluorine-containing compound represented by Formula (3) by successively reacting at least one chlorine-containing compound selected from the group consisting of the chlorine-containing fluoroalkane represented by Formula (1) and the chlorine-containing fluoroolefin represented by Formula (2) contained in the reactor inlet gas obtained in step (b) in the presence of a fluorination catalyst.

Item 12: The method for producing a fluorine-containing compound according to Item 11, wherein step (b) comprises a step of adjusting the concentration of the hydrogen chloride in the reactor inlet gas to not less than 0.01 vol % and not more than 3 vol %.

Item 13: The method for producing a fluorine-containing compound according to Item 11 or 12, wherein the chlorine-containing compound selected from the group consisting of the chlorine-containing fluoroalkane represented by Formula (1) and the chlorine-containing fluoroolefin represented by Formula (2) is 2-chloro-3,3,3-trifluoropropene.

Item 14: The method for producing a fluorine-containing compound according to any one of Items 11 to 13, wherein the fluorine-containing compound is 2,3,3,3-tetrafluoropropene.

Item 15: The method for producing a fluorine-containing compound according to any one of Items 11 to 13, wherein the chlorine-containing compound selected from the group consisting of the chlorine-containing fluoroalkane represented by Formula (1) and the chlorine-containing fluoroolefin represented by Formula (2) is 2-chloro-3,3,3-trifluoropropene, and the fluorine-containing compound is 1,1,1,2,2-pentafluoropropane or 2,3,3,3-tetrafluoropropene.

Item 16: The method for producing a fluorine-containing compound according to any one of Items 11 to 15, wherein, in step (a), the concentration of the hydrogen chloride in the reactor inlet gas is not less than 0.01 vol % and not more than 200 vol %, based on the total amount of the chlorine-containing alkane represented by Formula (4), the chlorine-containing olefin represented by Formula (5), and the chlorine-containing olefin represented by Formula (6).

Advantageous Effects of Invention

The production method of the present invention is a method for producing a fluorine-containing compound represented by Formula (3): $CF_3CFY_nCH_2Z_n$ (wherein n is 0 or 1, one of Y and Z is H, and the other is F or Cl) by successively reacting at least one chlorine-containing compound selected from the group consisting of chlorine-containing fluoroalkane represented by Formula (1): $CX_3CHClCH_2Cl$ (wherein X is independently F or Cl, with the proviso that at least one X is F) and chlorine-containing fluoroolefin represented by Formula (2): $CX_3CCl=CH_2$ (wherein X is independently F or Cl, with the proviso that at least one X is F) with anhydrous hydrogen fluoride in the presence of a fluorination catalyst, while ensuring high conversion of the starting compound, reducing production of by-products such as an overly fluorinated compound, and reducing equipment costs and energy costs.

BRIEF DESCRIPTION OF DRAWINGS

The FIGURE is a flow chart of an example of the reaction process in the present invention.

DESCRIPTION OF EMBODIMENTS

The present invention is described in detail below. The major propanes and propenes relating to the present invention are defined in Table 1.

TABLE 1

| Code | Chemical Name | Chemical Formula |
|---|---|---|
| 1234yf | 2,3,3,3-tetrafluoropropene | $CF_3CF{=}CH_2$ |
| 240db | 1,1,1,2,3-pentachloropropane | $CCl_3CHClCH_2Cl$ |
| 245cb | 1,1,1,2,2-pentafluoropropane | $CF_3CF_2CH_3$ |
| 1230xa | 1,1,2,3-tetrachloropropene | $CH_2ClCCl{=}CCl_2$ |
| 1233xf | 2-chloro-3,3,3-trifluoropropene | $CF_3CCl{=}CH_2$ |

Reaction Step

An example of the embodiment of the present invention is a method for producing a fluorine-containing compound represented by Formula (3): $CF_3CFY_nCH_2Z_n$ (wherein n is 0 or 1, one of Y and Z is H, and the other is F or Cl) by successively reacting at least one chlorine-containing compound selected from the group consisting of chlorine-containing fluoroalkane represented by Formula (1): $CX_3CHClCH_2Cl$ (wherein X is independently F or Cl, with the proviso that at least one X is F) and chlorine-containing fluoroolefin represented by Formula (2): $CX_3CCl{=}CH_2$ (wherein X is independently F or Cl, with the proviso that at least one X is F) with anhydrous hydrogen fluoride in the presence of a fluorination catalyst. The method is characterized in that the reactor inlet gas contains hydrogen chloride at a specific concentration.

The chlorine-containing compound is not particularly limited insofar as the compound falls within the range represented by Formula (1) or (2); however, 243db, 1233xf, and the like are preferable, and 1233xf is particularly preferable.

Further, the fluorine-containing compound is not particularly limited insofar as the compound falls within the range represented by Formula (3); however, 1234yf is preferable.

An example of another embodiment of the present invention is a method for producing a fluorine-containing compound represented by Formula (3): $CF_3CFY_nCH_2Z_n$ (wherein n is 0 or 1, one of Y and Z is H, and the other is F or Cl) by reacting at least one chlorine-containing compound selected from the group consisting of chlorine-containing fluoroalkane represented by Formula (1): $CX_3CHClCH_2Cl$ (wherein X is independently F or Cl, with the proviso that at least one X is F) and chlorine-containing fluoroolefin represented by Formula (2): $CX_3CCl{=}CH_2$ (wherein X is independently F or Cl, with the proviso that at least one X is F) with anhydrous hydrogen fluoride in the presence of a fluorination catalyst, the method further comprising separating a component containing unreacted raw material from a reactor outlet gas and circulating the component in the reactor inlet to subject the component again to the reaction, wherein the concentration of hydrogen chloride in the circulating gas is not less than 0.01 vol % and not more than 10 vol %.

The chlorine-containing compound is not particularly limited insofar as the compound falls within the range represented by Formula (1) or (2); however, 243db, 1233xf, and the like are preferable, and 1233xf is particularly preferable.

The fluorine-containing compound is not particularly limited insofar as the compound falls within the range represented by Formula (3); however, 244bb, 1234yf, and the like are preferable, and 1234yf is particularly preferable.

An example of another embodiment of the present invention is a method for producing a fluorine-containing compound comprising:

(a) obtaining a reactor outlet gas containing at least one chlorine-containing compound selected from the group consisting of chlorine-containing fluoroalkane represented by Formula (1) and chlorine-containing fluoroolefin represented by Formula (2) and hydrogen chloride by reacting at least one chlorine-containing compound selected from the group consisting of chlorine-containing alkane represented by Formula (4): $CX_3CHClCH_2Cl$ (wherein X is independently F or Cl, with the proviso that at least one X is Cl), chlorine-containing olefin represented by Formula (5): $CX_3CCl{=}CH_2$ (wherein X is independently F or Cl, with the proviso that at least one X is Cl), and chlorine-containing olefin represented by Formula (6): $CX_2{=}CClCH_2X$ (wherein X is independently F or Cl, with the proviso that at least one X is Cl) with anhydrous hydrogen fluoride in the presence of a fluorination catalyst;

(b) adjusting the concentration of the hydrogen chloride in the reactor outlet gas obtained in step (a) to not less than 0.01 vol % and not more than 10 vol % to obtain a reactor inlet gas to be subjected to a reactor for obtaining a fluorine-containing compound represented by Formula (3); and (c) producing the fluorine-containing compound represented by Formula (3) by successively reacting at least one chlorine-containing compound selected from the group consisting of the chlorine-containing fluoroalkane represented by Formula (1) and the chlorine-containing fluoroolefin represented by Formula (2) contained in the reactor inlet gas obtained in step (b) in the presence of a fluorination catalyst.

The chlorine-containing fluoroalkane represented by Formula (1) and the chlorine-containing fluoroolefin represented by Formula (2) are not particularly limited insofar as the compound of Formula (4), (5), or (6) may be obtained as a raw material; however, 1233xf is preferable.

Further, the fluorine-containing compound is not particularly limited insofar as the compound falls within the range represented by Formula (3); however, 244bb, 1234yf, and the like are preferable, and 1234yf is particularly preferable.

Further, in step (a), the reactor inlet gas may contain hydrogen chloride, and the concentration of hydrogen chloride is preferably not less than 0.01 vol % and not more than 200 vol %, based on the total amount of the chlorine-containing alkane represented by Formula (4), the chlorine-containing olefin represented by Formula (5), and the chlorine-containing olefin represented by Formula (6).

Hydrogen Chloride

The production method according to an embodiment of the present invention comprises incorporating hydrogen chloride in the reactor inlet gas.

The method for incorporating hydrogen chloride in the reactor inlet gas is not particularly limited. For example, the following methods may be used: a method comprising supplying a starting material to a reactor beforehand and further adding hydrogen chloride thereto, or a method comprising supplying a starting material and hydrogen chloride to a reactor simultaneously. Alternatively, hydrogen chloride may be supplied to a reactor beforehand, and then a starting material may be supplied to the reactor.

When hydrogen chloride is supplied to a reactor, hydrogen chloride may be supplied from any part of the reactor. For example, when a raw material is reacted using a method of continuously supplying the raw material from the inlet of a reactor to perform fluorination in the reactor, and then continuously discharging the product from the outlet of the reactor ("continuous reaction mode"), hydrogen chloride is preferably supplied from the inlet of the reactor. When hydrogen chloride is supplied from the inlet of a reactor, the generation of overly fluorinated compounds is likely to be reduced, and a fluorine-containing compound represented by Formula (3) (e.g., 1234yf) in particular can be efficiently produced. Even in the continuous reaction mode, the order of supplying the starting material and hydrogen chloride is not particularly limited. After the starting material is supplied, hydrogen chloride may be supplied, or both may be supplied to a reactor simultaneously. However, from the standpoint of further reduced generation of overly fluorinated compounds, it is preferable to supply both to the reactor simultaneously.

The concentration of hydrogen chloride in the reactor inlet gas is not less than 0.01 vol % and not more than 10 vol %. When the concentration of hydrogen chloride in the reactor inlet gas falls within this range, the generation of overly fluorinated compounds as by-products is sufficiently reduced, and cumbersome steps in deacidification of the reaction outlet gas are not required. It is sufficient that the concentration of hydrogen chloride in the reactor inlet gas is not less than 0.01 vol % and not more than 10 vol %; however, the concentration of hydrogen chloride is preferably not less than 0.01 vol % and not more than 3 vol %. Ensuring a state substantially free of hydrogen chloride requires large equipment costs and energy costs for removing hydrogen chloride before the reaction, and is thus not economical. On the other hand, if the amount of hydrogen chloride is too large, the conversion of the reactant decreases, thereby decreasing productivity.

Hydrogen chloride is generated when the chlorine-containing fluoroalkane or the chlorine-containing fluoroolefin contained in the starting material is fluorinated. However, such generation of hydrogen chloride occurs in order from the inlet of the reactor or the inlet of the reactive site such as the catalyst layer. Unless hydrogen chloride is separately supplied to the reactor as described above, hydrogen chloride becomes almost absent around the inlet of the reactor, thus facilitating the excessive fluorination of the product around the inlet. This means that the hydrogen chloride generated during fluorination of the starting material is unlikely to contribute to reduction of overly fluorinated compounds.

Fluorinating Agent

The fluorination reaction of the chlorine-containing fluoroalkane or the chlorine-containing fluoroolefin contained in the starting material may be performed using a fluorinating agent either in the presence or absence of a catalyst.

Hydrogen fluoride is preferably used as the fluorinating agent. When fluorination reaction is performed in the presence of a catalyst, the type of the catalyst is not particularly limited. Catalysts traditionally used in fluorination reaction of halogenated hydrocarbons may be used. For example, known materials traditionally used in this reaction as a catalyst may be used. Examples of such materials include halides and oxides of transition metals, the elements of group 14, and the elements of group 15. Before performing a fluorination reaction, the reactor may be packed with a catalyst.

Typically, it is suitable that the amount of the fluorinating agent is about 1 to 100 mol per mol of the chlorine-containing fluoroalkane and the chlorine-containing fluoroolefin, and the amount of the fluorinating agent may be about 5 to 50 mol per mol of the chlorine-containing fluoroalkane or the chlorine-containing fluoroolefin.

When the fluorinating agent, or pentachloropropane and tetrachloropropene, are supplied to a reactor, a gas inert to the raw material and the catalyst, such as nitrogen, helium, or argon, may also be present. When the starting material is supplied to a reactor, an oxidizer such as oxygen or chlorine may be supplied together.

The reactor is preferably a tubular reactor. The method for contacting the starting material with the catalyst is preferably a fixed bed technique. The reactor is preferably made from a material resistant to the corrosive action of hydrogen fluoride.

Catalyst

The reaction may be performed in either a liquid phase or gas phase, and is preferably performed in a gas phase. In the use of a gas phase, hydrogen chloride can reduce the generation of overly fluorinated compounds to a particularly greater degree.

When the reaction is performed in a gas phase, metal oxides, metal fluorides, or fluorinated metal oxides may be suitably used as a catalyst. A catalyst containing chromium or aluminum is particularly preferable. These catalysts may contain, as the second component, a metal component such as nickel, cobalt, zinc, copper, indium, manganese, or lanthanoid.

Further, these gas phase reaction catalysts may be supported or not supported by a carrier. When the catalyst is supported by a carrier, examples of preferable carriers include metal oxides and metal fluorides such as alumina, chromia, aluminum fluorides, and chromium fluorides.

The liquid phase reaction catalysts are also not particularly limited; however, preferable examples include metal halides, more preferably chlorides or fluorides of antimony, niobium, molybdenum, tin, tantalum, tungsten, and the like.

Reaction Conditions

The reaction temperature in the fluorination reaction is not particularly limited, and is generally about 200° C. to 550° C. The pressure during the fluorination reaction is also not particularly limited, and the reaction may be performed under reduced pressure, ordinary pressure, or increased pressure. Although the reaction may be generally carried out at pressure near atmospheric pressure (0.1 MPa), it can also proceed smoothly under reduced pressure of less than 0.1 MPa. Further, the reaction may be performed under increased pressure within a range in which the raw materials do not liquefy.

There is no limitation on the reaction time. For example, when catalyst is used, the contact time represented by W/F, i.e., the ratio of the amount of packed catalyst W(g) to the total flow rate $F_0$ (a flow rate at 0° C. and 0.1 MPa: cc/sec) of gas components supplied to the reaction system is preferably about 0.1 to 90 g·sec/cc, and more preferably about 1 to 50 g·sec/cc. When catalyst is not used, for example, the contact time represented by the ratio V/F, i.e., the ratio of volume V (cc) of the reactor to the total flow rate $F_o$ (flow rate at 0° C. and 0.1 MPa: cc/sec) of the gas components passed in the reaction system is preferably in the range of about 0.1 to 100 sec, and more preferably bout 1 to 30 sec.

In this case, the total flow rate of gas components means the total flow rate of raw material, hydrogen fluoride, and hydrogen chloride. When inert gas, oxygen, etc. are used, the total flow rate of gas components means the total flow rate also including the flow rates of these substances.

By performing the above fluorination reaction, the fluorine-containing compound represented by Formula (3) is produced. The structure of the fluorine-containing compound varies depending on the type of the chlorine-containing fluoroalkane or chlorine-containing fluoroolefin contained in the starting material.

Separation Step and Recycling Step

In the present invention, unreacted chlorine-containing compounds, fluorinating agents, intermediates, and hydrogen chloride and the like are separated from the product obtained in the above reaction step, and at least a part thereof is recycled and reused in the above reaction step. This separation step may be performed in an arbitrary manner, and may include multiple different separation steps. More specifically, the separation step may be distillation, liquid-liquid separation, extractive distillation, liquid-liquid extractive separation, or a combination of these steps. These steps are merely examples, and do not limit the separation step to carry out the present invention. In one embodiment of the present invention, the concentration of the hydrogen chloride in the circulating gas is not less than 0.01 vol % and not more than 10 vol %, preferably not less than 0.01 vol % and not more than 3 vol %.

In one embodiment of the present invention, the concentration of the hydrogen chloride in the reactor outlet gas obtained in step (a) is adjusted so that the concentration falls within a range of not less than 0.01 vol % and not more than 10 vol %, preferably not less than 0.01 vol % and not more than 3 vol %.

When a fraction obtained in the separation step is recycled and reused, an acid removal step, a moisture removal step, a crude purification step such as distillation, and the like may be performed if necessary. The conditions in these steps may be appropriately set depending on the components to be separated.

When distillation is used in the separation step, the following is a specific example of the conditions when 1234yf is produced as a fluorine-containing compound and hydrogen fluoride is used as the fluorinating agent in the reaction step.

The conditions in the separation of 1234yf from the components that are obtained from the reactor outlet components in the reaction step and to be recycled and reused in the reaction step may be conditions that enable separation of unreacted raw material, hydrogen fluoride, intermediates, and the like as high-boiling-point components, and separation of 1234yf, hydrogen chloride, and the like as low-boiling-point components. Since the chlorine-containing compound raw material and the intermediates in the present invention have boiling points higher than that of the desired 1234yf, the high-boiling-point components thus separated may be recycled and reused in the reaction step. The components that cannot be used as intermediates of 1234yf contained in the high-boiling-point components may be isolated from the components to be recycled by being subjected to another separation step before the components are circulated to the reaction step. Further, the components that cannot be used as intermediates of 1234yf can be isolated and removed from the components to be recycled and reused also in view of suppressing degradation of the catalyst used in the reaction step.

The components containing 1234yf and hydrogen chloride and the like separated as low-boiling-point components can further be subjected to any purification step, such as single- or multi-stage distillation, liquid separation, extraction, or extractive distillation, to separate and collect 1234yf. For example, when a distillation operation is performed as a separation means, high-purity 1234yf can be collected through a single- or multi-stage distillation step from the bottom or a middle portion of the final distillation column, and hydrogen chloride can be collected from the top of the distillation column and reused for the desired purpose. Other organic components contained in the hydrogen chloride-containing fraction are chlorine-containing fluorides, which can be used as intermediates in the reaction step. Thus, these organic components can be separated from other components in the step of collecting 1234yf, and can be recycled and reused in the reaction step. In one embodiment of the present invention, the concentration of the hydrogen chloride in the circulating gas is not less than 0.01 vol % and not more than 10 vol %, preferably not less than 0.01 vol % and not more than 3 vol %.

Further, when oxygen is introduced in the reaction step so as to retain the duration of life of the catalyst, the hydrogen chloride-containing fraction contains oxygen, which may be recycled and reused in the reaction step.

Actions

Since the production method according to an embodiment of the present invention comprises the step of incorporating hydrogen chloride in the reactor inlet gas in the reactor where the fluorination reaction of the starting material is performed, the generation of overly fluorinated compounds as by-products is reduced. Thus, fluorine-containing compound represented by Formula (3), such as 1233xf and 1234yf, are produced at a high yield. Conversely, if the fluorination reaction is performed without the step of incorporating hydrogen chloride in the reactor inlet gas in the reactor where the fluorination reaction of the starting material is performed, for example, overly fluorinated compounds such as 245cb are more easily generated as by-products.

As described above, since the generation of overly fluorinated compounds as by-products can be reduced in the production method according to this embodiment, the selectivity for the target product obtained from the starting material can be increased, thereby producing the desired fluorine-containing compound of high purity at a high yield.

In one embodiment of the present invention, in step (a), hydrogen chloride may be incorporated in the reactor inlet gas, and the concentration of the hydrogen chloride is preferably not less than 0.01 vol % and not more than 200 vol %, based on the total amount of the chlorine-containing alkane represented by Formula (4), the chlorine-containing olefin represented by Formula (5), and the chlorine-containing olefin represented by Formula (6). When a pentachloroalkane such as 240db is used as a starting material in step (a), the pentachloroalkane is dehydrochlorinated in a reaction tube, thus becoming prone to conversion into a tetrachloropropene. Further, this tetrachloropropene more easily causes catalyst degradation than the pentachloropropane. However, because, in the production method in this embodiment, hydrogen chloride is supplied to the reactor in which a fluorination reaction is performed as described above, the dehydrochlorination is suppressed due to chemical equilibrium. Thus, even in the use of a pentachloropropane as a starting material, the conversion of the pentachloropropane into a tetrachloropropene caused by dehydrochlorination is reduced. This lowers the risk of catalyst degradation caused by the tetrachloropropene, thus further improving the life of the catalyst. As described above, from the standpoint of improving the life of the catalyst for use in the fluorination reaction, it is preferable to use a pentachloropropane, such as 240db, as a starting material.

As described above, the embodiment of the present invention enables production while ensuring high conversion of the starting compound, reducing production of by-products such as overly fluorinated compounds, and reducing equipment costs and energy costs. This is presumably because the incorporation of hydrogen chloride in the reaction gas inhibits over-fluorination.

EXAMPLES

The present invention is more specifically explained below with reference to Examples. However, the present invention is not limited to these Examples.

Example 1

11.1 g of a chromium oxide catalyst was placed in a tubular reactor, and a fluorination reaction was performed at a reaction temperature of 365° C. under atmospheric pressure by supplying anhydrous hydrogen fluoride gas, oxygen gas, hydrogen chloride gas, and 1233xf gas. The flow rates of the gases are as follows: anhydrous hydrogen fluoride gas=60.0 Nml/min, oxygen gas=0.1 Nml/min, hydrogen chloride gas=0.1 Nml/min, and 1233xf=6.0 Nml/min.

After about 20 hours, the gas that flowed from the reactor was analyzed by gas chromatography. The conversion of 1233xf was 18%. The production ratio between 1234yf and 245cb was 81:19.

Example 2

The same fluorination reaction as in Example 1 was performed except that the flow rate of the hydrogen chloride gas to be supplied was 0.6 Nml/min. After about 20 hours, the gas that flowed from the reactor was analyzed by gas chromatography. The conversion of 1233xf was 16%. The production ratio between 1234yf and 245cb was 79:21.

Example 3

The same fluorination reaction as in Example 1 was performed except that the flow rate of the hydrogen chloride gas to be supplied was 1.0 Nml/min. After about 20 hours, the gas that flowed from the reactor was analyzed by gas chromatography. The conversion of 1233xf was 12%. The production ratio between 1234yf and 245cb was 83:17.

Example 4

The same fluorination reaction as in Example 1 was performed except that the flow rate of the hydrogen chloride gas to be supplied was 5.3 Nml/min. After about 20 hours, the gas that flowed from the reactor was analyzed by gas chromatography. The conversion of 1233xf was 8%. The production ratio between 1234yf and 245cb was 85:15.

Comparative Example 1

The same fluorination reaction as in Example 1 was performed except that supply of the hydrogen chloride gas was stopped. After about 20 hours, the gas that flowed from the reactor was analyzed by gas chromatography. The conversion of 1233xf was 18%. The production ratio between 1234yf and 245cb was 78:22.

TABLE 2

| | HCl Amount at Reactor Inlet | Conversion of 1233xf | Production Ratio between 1234yf:245cb |
|---|---|---|---|
| Example 1 | 0.15 vol % | 18% | 81:19 |
| Example 2 | 0.90 vol % | 16% | 79:21 |
| Example 3 | 1.5 vol % | 12% | 83:17 |
| Example 4 | 7.4 vol % | 8% | 85:15 |
| Comparative Example 1 | — | 18% | 78:22 |

The invention claimed is:

1. A method for producing a fluorine-containing compound of Formula (3):
   $CF_3CFYCH_2Z$, wherein n is 0 or 1, one of Y and Z is H, and the other is F or Cl, by successively reacting at least one chlorine-containing compound selected from the group consisting of chlorine-containing fluoroalkane of Formula (1): $CX_3CHClCH_2Cl$, wherein X is independently F or Cl, with the proviso that at least one X is F; and chlorine-containing fluoroolefin of Formula (2): $CX_3CC\!\!=\!\!CH_2$, wherein X is independently F or Cl, with the proviso that at least one X is F, with anhydrous hydrogen fluoride in the presence of a fluorination catalyst, wherein a reactor inlet gas comprises hydrogen chloride in a concentration of not less than 0.15 vol % and not more than 10 vol %.

2. The method for producing a fluorine-containing compound according to claim 1, wherein the concentration of hydrogen chloride in the reactor inlet gas is not less than 0.15 vol % and not more than 3 vol %.

3. The method for producing a fluorine-containing compound according to claim 1, wherein the chlorine-containing compound is at least one compound selected from the group consisting of 2,3-dichloro-1,1,1-trifluoropropane and 2-chloro-3,3,3-trifluoropropene, and the fluorine-containing compound is 1,1,1,2,2-pentafluoropropane, 1,1,1,2,3-pentafluoropropane, or 2,3,3,3-tetrafluoropropene.

4. The method for producing a fluorine-containing compound according to claim 1, wherein the chlorine-containing compound is 2-chloro-3,3,3-trifluoropropene.

5. The method for producing a fluorine-containing compound according to claim 1, wherein the fluorine-containing compound is 2,3,3,3-tetrafluoropropene.

6. A method for producing a fluorine-containing compound of Formula (3): $CF_3CFYCH_2Z$, wherein n is 0 or 1, one of Y and Z is H, and the other is F or Cl, by reacting at least one chlorine-containing compound selected from the group consisting of chlorine-containing fluoroalkane of Formula (1): $CX_3CHClCH_2Cl$, wherein X is independently F or Cl, with the proviso that at least one X is F; and chlorine-containing fluoroolefin of Formula (2): $CX_3CCl\!\!=\!\!CH_2$, wherein X is independently F or Cl, with the proviso that at least one X is F, with anhydrous hydrogen fluoride in the presence of a fluorination catalyst, the method further comprising separating a component containing unreacted raw material from a reactor outlet gas and circulating the component in the reactor inlet to subject the component again to the reaction, wherein a circulating gas comprises hydrogen chloride in a concentration of not less than 0.15 vol % and not more than 10 vol %.

7. The method for producing a fluorine-containing compound according to claim 6, wherein the concentration of hydrogen chloride in the circulating gas is not less than 0.15 vol % and not more than 3 vol %.

8. The method for producing a fluorine-containing compound according to claim 6, wherein the chlorine-containing compound is at least one compound selected from the group consisting of 2,3-dichloro-1,1,1-trifluoropropane and 2-chloro-3,3,3-trifluoropropene, and the fluorine-containing compound is 1,1,1,2-tetrafluoro-2-chloropropane, 1,1,1,2,2-pentafluoropropane, or 2,3,3,3-tetrafluoropropene.

9. The method for producing a fluorine-containing compound according to claim 6, wherein the chlorine-containing compound is 2-chloro-3,3,3-trifluoropropene.

10. The method for producing a fluorine-containing compound according to claim 6, wherein the fluorine-containing compound is 2,3,3,3-tetrafluoropropene.

11. A method for producing a fluorine-containing compound comprising the steps of: (a) obtaining a reactor outlet gas containing at least one chlorine-containing compound selected from the group consisting of chlorine-containing fluoroalkane of Formula (1): $CX_3CHClCH_2Cl$, wherein X is independently F or Cl, with the proviso that at least one X is F; and chlorine-containing fluoroolefin of Formula (2): $CX_3CCl=CH_2$, wherein X is independently F or Cl, with the proviso that at least one X is F, and hydrogen chloride by reacting at least one chlorine-containing compound selected from the group consisting of chlorine-containing alkane of Formula (4): $CX_3CHClCH_2Cl$, wherein X is independently F or Cl, with the proviso that at least one X is Cl; chlorine-containing olefin of Formula (5): $CX_3CCl=CH_2$, wherein X is independently F or Cl, with the proviso that at least one X is Cl; and chlorine-containing olefin of Formula (6): $CX_2=CClCH_2X$, wherein X is independently F or Cl, with the proviso that at least one X is Cl, with anhydrous hydrogen fluoride in the presence of a fluorination catalyst; (b) adjusting the concentration of the hydrogen chloride in the reactor outlet gas obtained in step (a) to not less than 0.15 vol % and not more than 10 vol % to obtain a reactor inlet gas to be subjected to a reactor for obtaining a fluorine-containing compound of Formula (3): $CF_3CFY_nCH_2Z_n$, wherein n is 0 or 1, one of Y and Z is H, and the other is F or Cl; and (c) producing the fluorine-containing compound of Formula (3) by successively reacting at least one chlorine-containing compound selected from the group consisting of the chlorine-containing fluoroalkane of Formula (1) and the chlorine-containing fluoroolefin of Formula (2) contained in the reactor inlet gas obtained in step (b) in the presence of a fluorination catalyst.

12. The method for producing a fluorine-containing compound according to claim 11, wherein step (b) comprises a step of adjusting the concentration of the hydrogen chloride in the reactor inlet gas to not less than 0.15 vol % and not more than 3 vol %.

13. The method for producing a fluorine-containing compound according to claim 11, wherein the chlorine-containing compound selected from the group consisting of the chlorine-containing fluoroalkane of Formula (1) and the chlorine-containing fluoroolefin of Formula (2) is 2-chloro-3,3,3-trifluoropropene.

14. The method for producing a fluorine-containing compound according to claim 11, wherein the fluorine-containing compound is 2,3,3,3-tetrafluoropropene.

15. The method for producing a fluorine-containing compound according to claim 11, wherein the chlorine-containing compound selected from the group consisting of the chlorine-containing fluoroalkane of Formula (1) and the chlorine-containing fluoroolefin of Formula (2) is 2-chloro-3,3,3-trifluoropropene, and the fluorine-containing compound is 1,1,1,2,2-pentafluoropropane or 2,3,3,3-tetrafluoropropene.

16. The method for producing a fluorine-containing compound according to claim 11, wherein, in step (a), the concentration of the hydrogen chloride in a reactor inlet gas is not less than 0.15 vol % and not more than 200 vol %, based on the total amount of the chlorine-containing alkane of Formula (4), the chlorine-containing olefin of Formula (5), and the chlorine-containing olefin of Formula (6).

* * * * *